(12) United States Patent
Foster

(10) Patent No.: US 9,497,911 B2
(45) Date of Patent: Nov. 22, 2016

(54) WILD RICE CULTIVAR KC-755

(71) Applicant: KENNAN CORPORATION, Pleasant Grove, CA (US)

(72) Inventor: Ken Wood Foster, Davis, CA (US)

(73) Assignee: KENNAN CORPORATION, Pleasant Grove, CA (US)

( * ) Notice: Subject to any disclaimer, the term of this patent is extended or adjusted under 35 U.S.C. 154(b) by 316 days.

(21) Appl. No.: 14/184,808

(22) Filed: Feb. 20, 2014

(65) Prior Publication Data

US 2015/0230422 A1 Aug. 20, 2015

(51) Int. Cl.
*A01H 5/10* (2006.01)

(52) U.S. Cl.
CPC ..................................... *A01H 5/10* (2013.01)

(58) Field of Classification Search
None
See application file for complete search history.

(56) References Cited

U.S. PATENT DOCUMENTS

| | | | |
|---|---|---|---|
| 5,304,719 A | 4/1994 | Segebart | |
| 5,367,109 A | 11/1994 | Segebart | |
| 5,523,520 A | 6/1996 | Hunsperger et al. | |
| 5,763,755 A | 6/1998 | Carlone | |
| 5,773,680 A * | 6/1998 | Foster | A01H 5/10 800/274 |
| 5,850,009 A | 12/1998 | Kevern | |
| 5,955,648 A | 9/1999 | Foster et al. | |
| 6,956,154 B2 | 10/2005 | Xie | |
| 7,301,083 B2 | 11/2007 | Sarreal et al. | |

OTHER PUBLICATIONS

Oelke et al, 1997, Cereal Foods World, 42:234-247.*
Bennetzen, et al., 1992, Approaches and progress in the molecular cloning of plant disease resistance genes, *Genetic Engineering*, 14:99-124.
DeBolle, et al., 1996, Antimicrobial peptides from *Mirabilis jalapa* and *Amaranthus caudatus*: expression, processing, localization and biological activity in transgenic tobacco, *Plant Molec. Biol.*, 31:993-1008.
Duvall, et al., 1988, Nonreciprocal Hybridization Failure in Crosses Between Wild-Rice Species (*Zizania palustris* X *Z. aquatica*: Poaceae), Systematic Botany, vol. 13, pp. 229-334.
Emerging Food R&D Report, 1994, Food Technology Intelligence, Inc., Information Access Company, IAC Newsletter Database, 'Novel hybrids expand market possibilities for wild rice', 1 page.
Eshed, et al., 1996, Less-than-additive epistatic interactions of quantitative trait loci in tomato, *Genetics*, 143:1807-1817.
Forsberg, et al., 1980, Sources, Maintenance, and Utilization of Parental Material, In: Hybridization of Crop Plants, American Society of Agronomy-Crop Science, WI, pp. 65-81.
Foster, et al., 1980, Genetic Variation of Four Traits in a Population of Zizania Aquatica, *Can J. Plant Sci.*, 60:1-4.
Hayashi, et al., 1988, Hybrids of Rice (*Oryza sativa* L.) and Wild Oryza Species Obtained by Cell Fusion, *Molecular and General Genetics*, vol. 214, pp. 6-10.
Kahler, et al., 2014, Maintaining Food Value of Wild Rice (*Zizania palustris* L.) Using Comparative Genomics, Chapter 9, pp. 233-248 In Tuberosa, et al., Genomics of Plant Genetics Resources, vol. 2, Crop Productivity, Food Security, and Nutritional Quality, Springer Science.
Kraft, et al., 2000, Linkage disequilibrium and fingerprinting in sugar beet, *Theor. Appl. Genet.*, 101:323-326.
Oelke, et al., 1997, Wild Rice—new interest in an old crop, *Cereal Foods World*, vol. 42, pp. 234-247.
Pang, et al., 1992, Expression of a gene encoding a scorpion insectotoxin peptide in yeast, bacteria and plants, *Gene*, 116:165-172.
Poehlman, J.M. and Sleper, D.A., Breeding Field Crops, 4th Ed. 1995, Iowa State University Press, p. 473.
Porter, R.A., Wildrice Varietal Trials Results, Jan. 2007, Minnesota Agricultural Experiment Station, University of Minnesota, pp. 51-52.
Porter, R., Wildrice Varietal Trials Results, Jan. 2008, Minnesota Agricultural Experiment Station, University of Minnesota, pp. 50-51.
Porter, R., Wildrice Varietal Trials Results, Jan. 2012, Minnesota Agricultural Experiment Station, University of Minnesota, pp. 49-50.
Smith, C.W. and Dilday, R.H., Origin, Domestication, and Diversification in Rice: Origin, History, Technology, and Production, 2003, John Wiley & Sons, Inc., pp. 4-6.
Yu, et al., 1997, Importance of epistasis as the genetic basis of heterosis in an elite rice hybrid, *Proc. Natl. Acad. Sci.*, 94:9226-9231.

* cited by examiner

*Primary Examiner* — Jason Deveau Rosen
(74) *Attorney, Agent, or Firm* — Jondle & Associates, P.C.

(57) ABSTRACT

A wild rice cultivar designated KC-755 is disclosed. The invention relates to the seeds of wild rice cultivar KC-755, to the plants of wild rice KC-755 and to methods for producing a wild rice plant produced by crossing the cultivar KC-755 with itself or another wild rice variety. The invention further relates to hybrid wild rice seeds and plants produced by crossing the cultivar KC-755 with another wild rice cultivar.

25 Claims, No Drawings

WILD RICE CULTIVAR KC-755

BACKGROUND OF THE INVENTION

The present invention relates to a new and distinctive wild rice cultivar, designated KC-755. All publications cited in this application are herein incorporated by reference.

Wild rice (*Zizania palustris* L. Dore) is an important cultivated specialty crop grown predominantly in California and Minnesota, and is the only species in *Zizania* cultivated as a grain. Domestication efforts have been ongoing in the U.S. for about 50 years (Oelke, 2011). Although a small amount is cultivated in Hungary, wild rice is predominantly a United States crop. Total world production of wild rice in 2012 was about 20 million processed pounds, mostly coming from 29,000 acres of U.S. production. Modest quantities of non-cultivated lake wild rice are also harvested in Minnesota, Canada, Oregon, and Idaho. Export demand is growing and wild rice is now being exported to many countries including, but not limited to France, Germany, England, Russia, Lithuania, Spain, and China.

Wild rice is traditionally used as an ingredient to add variety and contrast in flavor, texture, and color to grain based dishes (wild rice, pasta, etc). The wild rice grain is nutritious and is normally consumed as a whole grain. It is considered a desirable part of a healthy diet as specified by the USDA Plate (www.choosemyplate.govfood-groups/grains.html). Wild rice is high in protein, dietary fiber, and iron (Timm and Slavin, 2013), and is gluten-free, low in fat, low in calories, and contains no cholesterol. Wild rice also contains antioxidant activity that has been found to be 30 times greater than white wild rice (Wu, et al. 1994; Yang, et al., 1994), and has a low glycemic index.

Consumption of processed wild rice currently stands at approximately 20 million lb/year worldwide. Consumption in the U.S. has stagnated while consumption world-wide is on the rise. Because it is a specialty crop, the price of wild rice remains higher than typical other whole grains, such as brown wild rice, whole grain barley, buckwheat, or quinoa. Although highly nutritious, being a specialty crop can also negatively affect the consumption of wild rice during difficult economic times. As it is not a food "staple," wild rice is easily foregone during economic downturns, as has been the case during the 2008-12 recession. Domesticating wild rice is ultimately important as it has the potential of becoming another whole grain "staple" with which to feed the growing world population. In order to do this, wild rice needs to become economically competitive with the growing of other whole grain crops, particularly rice.

One of the important steps required in the domestication of wild rice is the development of a superior variety. A superior wild rice variety needs to have improved yield capabilities for the grower, different kernel size characteristics for marketing, and the ability to maintain its genetic identity over time. Traditionally, wild rice varieties have produced poor yields due to a number of reasons: the plants were too tall (7-10 ft), they produced low levels of grain relative to plant matter, and they lodged under even moderate fertility and/or in bad weather. Varieties, such as 'Franklin' and 'Johnson,' originally from MN and adopted by California growers, were early examples of important, but poor yielding varieties. For example, in multi-location trials over a seven year period, four varieties averaged 1,660 kg/ha, green, in Minnesota (Porter, 2007).

Current wild rice varieties continue to have serious drawbacks in commercial production. Yield potential, even with hybrids, is limited by excessive height. This excessive height leads to low harvest index (excess allocation of dry matter to vegetative mass instead of grain), and to lodging susceptibility.

Therefore, it is desirable to develop a novel wild rice cultivar having superior traits, such as increased grain yield and increased kernel weight and kernel length, in order to improve consumer value and provide growers with a competitive wild rice crop.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary and illustrative, not limiting in scope. In various embodiments, one or more of the above described problems have been reduced or eliminated, while other embodiments are directed to other improvements.

According to the invention, there is provided a novel wild rice cultivar designated KC-755. This invention thus relates to the seeds of wild rice cultivar KC-755, to the plants of wild rice KC-755 and to methods for producing a wild rice plant produced by crossing the wild rice KC-755 with itself or another wild rice line.

Thus, any such methods using the wild rice variety KC-755 are part of this invention: selfing, backcrosses, hybrid production, crosses to populations, and the like. All plants produced using wild rice variety KC-755 as a parent are within the scope of this invention. Advantageously, the wild rice variety could be used in crosses with other, different, wild rice plants to produce first generation ($F_1$) wild rice hybrid seeds and plants with superior characteristics.

In another aspect, the present invention provides for single gene converted plants of KC-755. The single transferred gene may preferably be a dominant or recessive allele. Preferably, the single transferred gene will confer such traits as herbicide resistance, insect resistance, resistance for bacterial, fungal, or viral disease, male fertility, male sterility, enhanced nutritional quality, and industrial usage. The single gene may be a naturally occurring wild rice gene or a transgene introduced through genetic engineering techniques.

In another aspect, the present invention provides regenerable cells for use in tissue culture of wild rice plant KC-755. The tissue culture will preferably be capable of regenerating plants having the physiological and morphological characteristics of the foregoing wild rice plant, and of regenerating plants having substantially the same genotype as the foregoing wild rice plant. Preferably, the regenerable cells in such tissue cultures will be embryos, protoplasts, meristematic cells, callus, pollen, leaves, anthers, root tips, flowers, seeds, panicles or stems. Still further, the present invention provides wild rice plants regenerated from the tissue cultures of the invention.

In addition to the exemplary aspects and embodiments described above, further aspects and embodiments will become apparent by study of the following descriptions.

DETAILED DESCRIPTION OF THE INVENTION

In the description and tables which follow, a number of terms are used. In order to provide a clear and consistent understanding of the specification and claims, including the scope to be given such terms, the following definitions are provided:

Abiotic stress. As used herein, abiotic stress relates to all non-living chemical and physical factors in the environment. Examples of abiotic stress include, but are not limited to, drought, flooding, salinity, temperature, and climate change.

Aggregate sheath spot. Is caused by the fungus *Rhizoctonia oryzae-sativae* (Sawada) Mordue (=*Ceratobasidium oryzae-sativae*). This disease causes sheath lesions and can reduce yield and grain quality.

Alkali Spreading Value. Indicator of gelatinization temperature and an index that measures the extent of disintegration of milled wild rice kernel in contact with dilute alkali solution. Standard long grains have 3 to 5 Alkali Spreading Value (intermediate gelatinization temperature). Standard medium and short grain wild rice have 6 to 7 Alkali Spreading Values (low gelatinization temperature).

Allele. Allele is any of one or more alternative forms of a gene, all of which alleles relate to one trait or characteristic. In a diploid cell or organism, the two alleles of a given gene occupy corresponding loci on a pair of homologous chromosomes.

Alter. The utilization of up-regulation, down-regulation, or gene silencing.

Apparent Amylose Percent. The most important grain characteristic that describes cooking behavior. The percentage of the endosperm starch of milled wild rice that is amylose. Amylose values will vary over environments.

Backcrossing. Backcrossing is a process in which a breeder repeatedly crosses hybrid progeny back to one of the parents, for example, a first generation hybrid $F_1$ with one of the parental genotypes of the $F_1$ hybrid.

Bakanae. Is caused by the fungus *Fusarium fujikuroi* Nirenberg (=*Gibberella fujikuroi*). It causes reduced seed germination and abnormal seedling elongation often followed by crown rot. Susceptibility of varieties is expressed as percent symptomatic plants.

Blanking %. Visual estimate or count of the percent of sterile florets (florets that are empty with no filled kernels) in the panicle. Blanking may be induced by high temperatures and/or by genetic incompatibility of the parents.

Breakdown. The peak viscosity minus the hot paste viscosity.

Breeding. The genetic manipulation of living organisms.

Cell. Cell as used herein includes a plant cell, whether isolated, in tissue culture or incorporated in a plant or plant part.

Combining ability. As used herein, refers to the ability or property of a line to produce a level of heterosis in hybrid or synthetic combinations.

Cross-pollination. Fertilization by the union of two gametes from different plants.

Cool Paste Viscosity. Viscosity measure of rice flour/water slurry after being heated to 95EC and uniformly cooled to 50EC (American Association of Cereal Chemist). Values less than 200 for cool paste indicate softer cooking types of rice.

Days to 50% heading. Average number of days from planting to the day when 50% of all panicles are exerted at least partially through the leaf sheath. A measure of maturity.

Diploid. A cell or organism having two sets of chromosomes.

Elongation. Cooked kernel elongation is the ratio of the cooked kernel length divided by the uncooked kernel length.

Embryo. The embryo is the small plant contained within a mature seed.

Essentially all the Physiological and Morphological Characteristics. A plant having essentially all the physiological and morphological characteristics means a plant having the physiological and morphological characteristics of the cultivar, except for the characteristics derived from the converted gene.

$F_\#$. The "F" symbol denotes the filial generation, and the # is the generation number, such as $F_1$, $F_2$, $F_3$, etc.

Final Viscosity. Viscosity at the end of the test or cold paste.

Gene. As used herein, "gene" refers to a unit of inheritance corresponding to DNA or RNA that code for a type of protein or for an RNA chain that has a function in the organism.

Gene Silencing. The interruption or suppression of the expression of a gene at the level of transcription or translation.

Genotype. Refers to the genetic constitution of a cell or organism.

Grain Length (L). Length of a wild rice grain is measured in millimeters.

Grain Width (W). Width of a wild rice grain is measured in millimeters.

Haploid. A cell or organism having one set of the two sets of chromosomes in a diploid.

Harvest Index (HI). Represents the proportion of aboveground dry matter that is allocated to grain. Unimproved cereals, realistically including even most cultivated wild rice, have low harvest indices in the range of 15-20%, while HI of modern rice and wheat varieties can exceed 40%. This increased portioning efficiency increases grain yield with the same inputs.

Harvest Moisture. The percent of moisture of the grain when harvested.

Heterosis. The term heterosis is the superiority of a hybrid or synthetic in vigor, grain yield, or other characteristics when compared to parental lines or a good commercial variety. Heterosis can be expressed as a trait difference (e.g. yield) between a given hybrid versus one parent of a hybrid which has the highest value for the trait, also known as High Parent Heterosis or versus the best competitive commercial variety.

Hot Paste Viscosity. Viscosity measure of rice flour/water slurry after being heated to 95EC. Lower values indicate softer and stickier cooking types of rice.

Hull. This is defined as the inedible portion of the wild rice grain, the lemma and palea. The hull completely encloses the kernel but is not attached and therefore removes easily in processing.

Hybrid. The term hybrid is intended to refer to first generation progeny from crossing two non-identical parental lines. Parental lines may be related, as production of a modified single cross, or unrelated. One line of a hybrid, the female, is either male sterile or emasculated. Only the female is harvested for use as commercial seed, so that a high proportion of the seed is actually hybrid as opposed to selfed.

Inbred line (IBL). An inbred line is a group or set of related plants reproduced by inbreeding which are phenotypically and genotypically similar and more or less true breeding.

Inbreeding coefficient. The likelihood that alleles are identical by descent. Values range from 0 (non-inbred) to 1.0 (completely inbred).

Kernel. The de-hulled, unmilled grain of wild rice.

Kernel weight. The weight of an individual de-hulled, unmilled grain of wild rice. We report this property at 10% moisture content, the approximate moisture at which wild rice is marketed.

Kernel width. The straight-line breath or distance perpendicular to the length of a de-hulled, unmilled wild rice grain.

Kernel length:kernel width (KL:KW) ratio. The ratio, as an indicator of kernel shape, of kernel length to kernel width.

Linkage. Refers to a phenomenon wherein alleles on the same chromosome tend to segregate together more often than expected by chance if their transmission was independent.

Linkage Disequilibrium. Refers to a phenomenon wherein alleles tend to remain together in linkage groups when segregating from parents to offspring, with a greater frequency than expected from their individual frequencies.

Locus. A defined segment of DNA.

Lodging. Means the tendency of plants to fall down or break over. Excessive plant height, and weak straw, especially when combined with wind and/or rain, increases the potential for lodging. High plant populations and high fertility exacerbate the tendency. Lodging is detrimental to grain yields because it destroys the light interception capability of a normal leaf canopy and may also damage vascular tissue if the bend is acute enough.

Nucleic Acid. An acidic, chainlike biological macromolecule consisting of multiple repeat units of phosphoric acid, sugar and purine and pyrimidine bases.

Nutraceutical. Refers to a food or food product that provides health and or medical benefits, including the prevention and treatment of disease. Such products may range from isolated nutrients, dietary supplements and specific diets to genetically engineered foods, herbal products, and processed foods such as cereals, soups and beverages.

1000 Grain Wt. The weight of 1000 wild rice grains as measured in grams. It can be for paddy, brown or milled wilD rice.

Peak Viscosity. The maximum viscosity attained during heating when a standardized instrument-specific protocol is applied to a defined rice flour-water slurry.

Pedigree. Refers to the lineage or genealogical descent of a plant.

Pedigree Distance. Relationship among generations based on their ancestral links as evidenced in pedigrees. May be measured by the distance of the pedigree from a given starting point in the ancestry.

Percent Identity. Percent identity as used herein refers to the comparison of the homozygous alleles of two wild rice varieties. Percent identity is determined by comparing a statistically significant number of the homozygous alleles of two developed varieties. For example, a percent identity of 90% between wild rice variety 1 and wild rice variety 2 means that the two varieties have the same allele at 90% of their loci.

Percent Similarity. Percent identity as used herein refers to the comparison of the homozygous alleles of two wild rice varieties. Percent identity is determined by comparing a statistically significant number of the homozygous alleles of two developed varieties. For example, a percent identity of 90% between wild rice variety 1 and wild rice variety 2 means that the two varieties have the same allele at 90% of their loci.

Plant. As used herein, the term "plant" includes reference to an immature or mature whole plant, including a plant from which seed, grain, or anthers have been removed. Seed or embryo that will produce the plant is also considered to be the plant.

Plant Height. Plant height measured in centimeters or inches is taken from soil surface to the tip of the extended panicle at harvest.

Plant Parts. As used herein, the term "plant parts" (or a wild rice plant, or a part thereof) includes but is not limited to protoplasts, leaves, stems, roots, root tips, anthers, pistils, seed, grain, embryo, pollen, ovules, cotyledon, hypocotyl, pod, flower, shoot, tissue, petiole, cells, meristematic cells, and the like.

Population. A population is a group or set of plants which reproduce by interpollinating each other, more or less at random. Said population may be non-inbred (F<0.25), partially inbred, (F=0.25-0.75) or highly inbred (F>0.75). A population may be created by selection from another population, relaxation of selection in a partially inbred line, or by intermating of related or unrelated lines, such as a synthetic variety. Once created, a population will have no further influx of outside genetic material.

Progeny. As used herein, includes an $F_1$ wild rice plant produced from the cross of two wild rice plants where at least one plant includes wild rice cultivar KC-755 and progeny further includes, but is not limited to, subsequent $F_2$, $F_3$, $F_4$, $F_5$, $F_6$, $F_7$, $F_8$, $F_9$, and $F_{10}$ generational crosses with the recurrent parental line.

Quantitative Trait Loci (QTL). Quantitative trait loci (QTL) refer to genetic loci that control to some degree numerically representable traits that are usually continuously distributed.

RVA Viscosity. Rapid Visco Analyzer is a widely used laboratory instrument to examine paste viscosity, or thickening ability of milled rice during the cooking process.

RVU. The RVA scale is measured in RVUs. This is the native viscosity unit of the RVA. 1 RVU is equivalent to 12 CP. CP equals "centipoises" which equals unit of viscosity (kg $s^{-1}$ $m^{-1}$) and 1 kg $s^{-1}$ $m^{-1}$ equals 1000 centipoises.

Regeneration. Regeneration refers to the development of a plant from tissue culture.

Semi-dwarf. As used herein, means plants of stature reduced by 10-40%. The height reduction may be due to one or more genes. Plant form is generally maintained and seedling vigor is acceptable. The useful mutants that created the Green Revolution in wheat and rice are in this category. The most useful semidwarf gene in rice has proven to be $sd_1$. To date, we have not observed the corresponding mutation in wild rice, although there are candidates with useful phenotypes. This gene codes acts to reduce stem internode length but has little effect on panicle size. The reduction in stem tissue while maintaining panicle size increases harvest index (HI).

Setback. Setback 1 is the final viscosity minus trough viscosity. Setback 2 is the final viscosity minus peak viscosity and is what is most commonly referred to for rice quality testing.

Sex ratio. Means relative allocation of reproductive effort to female versus male components. A high sex ratio indicates high degree of femaleness. Wild rice is monoecious with both female and male flowers on the same axis. The wild forms of *Zizania* have adapted to occasional or frequent occurrence of sparse population density by producing a super abundance of male flowers. Conversely, in cultivated stands of wild rice, pollination can be assured with much less "maleness" because pollen may only have to travel centimeters rather than meters to hundreds of meters to effect a pollination event. An important step in the domestication of wild rice will be the alteration of sex ratio in the direction of femaleness.

Single Gene Converted (Conversion). Single gene converted (conversion), also known as coisogenic plants, refers to plants which are developed by a plant breeding technique called backcrossing wherein essentially all of the desired morphological and physiological characteristics of a variety are recovered in addition to the single gene transferred into the variety via the backcrossing technique or via genetic engineering.

Stem Rot. Is caused by the fungus *Sclerotium oryzae* Cattaneo (=*Magnaporthe salvinii*). It produces sheath and stem lesions that can reduce yield and grain quality.

Synthetic variety. A synthetic variety results from the blending of two or more male fertile lines. The resulting variety is therefore a blend of hybrid seed and selfed seed. Increasing the number of lines that are used in a synthetic variety will increase the percentage of hybrid seed. However, increasing the number of lines also increases the number of possible cross combinations, some of which may be poor. Initial and successive generations of a synthetic are denoted as: Syn 0, Syn 1, Syn 2, etc.

Trough Viscosity. The minimum viscosity after the peak, normally occurring when the sample starts to cool.

Wild rice cultivar KC-755 has reduced plant height, increased kernel size, increased grain yield, improved straw strength, and improvements in plant type. The plant type improvements include more erect flag leaves, more acute branching of female inflorescence, and larger panicles relative to the rest of the plant. Wild rice cultivar KC-755 can be used in synthetic and hybrid varieties of wild rice.

Rice cultivar KC-755 has shown uniformity and stability in farmer's fields as described in the following variety description information. It has been self-pollinated a sufficient number of generations with careful attention to uniformity of plant type. The line has been increased with continued observation for uniformity.

Rice cultivar KC-755 has the following morphologic and other characteristics (based primarily on data collected in Sacramento Valley of California, Sutter and Butte Counties).

TABLE 1

VARIETY DESCRIPTION INFORMATION

Plant:

Grain type: Moderately long grain
Plant height: 180.0 cm to 185.0 cm
Plant color: RHS 134B; UCL: Strong yellowish green R: 34 G: 145 B: 67
Maturity:

Days to maturity (50% heading): 61
Days to harvest: 112
Culm:

Angle (degrees from perpendicular after flowering): 0
Length (soil level to top of extended panicle on main stem): 188.0 cm
Height class: Normal; medium height
Internode color (after flowering): RHS 155C; UCL: Greenish white R: 232 G: 226 B: 223
Strength (lodging resistance): Moderate
Flag leaf (at maturity):

Length: 33.4 cm
Width: 2.6 mm
Pubescence: Dense, short hairs
Leaf angle (after heading): 13.6°
Blade color (at heading): RHS 134B; UCL: Strong yellowish green R: 34 G: 145 B: 67
Basal leaf sheath color (at heading): RHS 134B; UCL: Strong yellowish green R: 34 G: 145 B: 67

TABLE 1-continued

VARIETY DESCRIPTION INFORMATION

Ligule:

Length (from base of collar to the tip, at late vegetative stage): 5.17 mm
Color (late vegetative stage): Membranous; RHS 155C; UCL: Greenish white R: 232 G: 226 B: 223
Shape: Jagged edge
Collar Color (late vegetative stage): Midrib is RHS 1C; UCL: Light greenish yellow R: 228 G: 220 B: 108, pale; faintly to slightly RHS 55A; UCL: Deep purplish pink R: 208 G: 55 B: 104 at the edges
Auricle Color (late vegetative stage): Absent
Panicle:

Length: 50.9 cm
Female:

Length: 26.3 cm
Branching angle: Appressed; 2.2°
Color: Pale translucent RHS 155B; UCL: Yellowish white R: 246 G: 234 B: 227 at heading, becoming RHS 200B; UCL: Grayish reddish brown R: 45 G: 27 B: 25 at maturity
Male:

Length: 24.7 cm
Branching angle: 22.2°
Color: RHS 67A; UCL: Strong purplish red R: 159 G: 27 B: 76 at heading; fading and drying near maturity
Secondary branching: Slight, both female and male
Peduncle length (near maturity, value): 84.7 cm
Peduncle length (near maturity, %): 45.2%
Exsertion (near maturity, value): 29.7 cm
Exsertion (near maturity, %): 36.0%
Shattering: Low
Threshability: Intermediate; ideal
Grain (spikelet):

Awns (after full heading): 4.4 cm long, densely barbed, pale green
Apiculus color (at maturity): RHS 200B; UCL: Grayish reddish brown R: 45 G: 27 B: 25; same as lemma
Stigma color: Pale cream
Lemma and palea color (at maturity): RHS 200B; UCL: Grayish reddish brown R: 45 G: 27 B: 25
Lemma pubescence: Pubescent on margins and ribs, increasing to tip
Palea pubescence: Pubescent on rib, increasing toward tip
Female spikelet sterility (at maturity): 3-5%
Grain (seed):

Seed coat color: RHS 147A; UCL: Moderate olive green R: 35 B: 44 G: 27
Endosperm type: Non-glutinous
Endosperm translucency: Translucent when raw milled
Endosperm chalkiness: 20-25% frequency chalky core in raw milled kernels
Scent: None
Shape class (length/width ratio):
Paddy:

Length: 18.2 mm
Width: 2.17 mm
L/W ratio: 8.39
1000 Grains: 39.2 g
Brown (unmilled):

Length: 11.1 mm
Width: 1.92 mm
L/W ratio: 5.78
1000 Grains: 32.6 g
Milling quality (% hulls): 12.3%
Milling yield (% whole kernel (head) wild rice to rough wild rice): N/A
Processing yield or "Recovery": 52-57% (finished marketable product as percentage of inbound green weight)
Gelatinization temperature type: N/A
Seedling vigor not related to low temperature: 4 (Scale 1-5 best)
Disease resistance:

Rice blast (*Pyricularia oryzae*): Susceptible to at least some, probably many, races
Stem rot (*Sclerotium oryzae*): Resistant This invention also is directed to methods for producing a wild rice plant by crossing a first parent wild rice plant with a second parent wild rice plant wherein either the first or second parent wild rice plant is a wild rice plant of the line KC-755. Further, both first and second parent wild rice plants can come from the wild rice cultivar KC-755. Still further, this invention also is directed to methods for producing a wild rice cultivar KC-755-derived wild rice plant by crossing wild rice cultivar KC-755 with a second wild rice plant and growing the progeny seed, and repeating the crossing and growing steps with the wild rice cultivar KC-755-derived plant from 0 to 7 times. Thus, any such methods using the wild rice cultivar KC-755 are part of this invention: selfing, backcrosses, hybrid production, crosses to populations, and the like. All plants produced using wild rice cultivar KC-755 as a parent are within the scope of this invention, including plants derived from wild rice cultivar KC-755. Advantageously, the wild rice cultivar is used in crosses with other, different, wild rice cultivars to produce first generation ($F_1$) wild rice seeds and plants with superior characteristics.

It should be understood that the cultivar can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which wild rice plants can be regenerated, plant calli, plant clumps and plant cells that are intact in plants or parts of plants, such as embryos, pollen, ovules, flowers, glumes, panicles, leaves, stems, roots, root tips, anthers, pistils and the like.

FURTHER EMBODIMENTS OF THE INVENTION

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years, several methods for producing transgenic plants have been developed, and the present invention, in particular embodiments, also relates to transformed versions of the claimed cultivar.

Culture for expressing desired structural genes and cultured cells are known in the art. Also as known in the art, wild rice is transformable and regenerable such that whole plants containing and expressing desired genes under regulatory control may be obtained. General descriptions of plant expression vectors and reporter genes and transformation protocols can be found in Gruber, et al., "Vectors for Plant Transformation", in *Methods in Plant Molecular Biology & Biotechnology* in Glich, et al., (Eds. pp. 89-119, CRC Press, 1993). Moreover GUS expression vectors and GUS gene cassettes are available from Clone Tech Laboratories, Inc., Palo Alto, Calif. while luciferase expression vectors and luciferase gene cassettes are available from Pro Mega Corp. (Madison, Wis.). General methods of culturing plant tissues are provided for example by Maki, et al., "Procedures for Introducing Foreign DNA into Plants" in *Methods in Plant Molecular Biology & Biotechnology*, Glich, et al., (Eds. pp. 67-88 CRC Press, 1993); and by Phillips, et al., "Cell-Tissue Culture and In-Vitro Manipulation" in *Corn & Corn Improvement*, 3rd Edition; Sprague, et al., (Eds. pp. 345-387 American Society of Agronomy Inc., 1988). Methods of introducing expression vectors into plant tissue include the direct infection or co-cultivation of plant cells with *Agrobacterium tumefaciens*, described for example by Horsch et al., *Science*, 227:1229 (1985). Descriptions of *Agrobacterium* vector systems and methods for *Agrobacterium*-mediated gene transfer are provided by Gruber, et al., supra.

Useful methods include but are not limited to expression vectors introduced into plant tissues using a direct gene transfer method such as microprojectile-mediated delivery, DNA injection, electroporation and the like. More preferably expression vectors are introduced into plant tissues using a microprojectile media delivery system with a biolistic device or using *Agrobacterium*-mediated transformation. Transformant plants obtained with the protoplasm of the invention are intended to be within the scope of this invention.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed wild rice plants, using transformation methods as described below to incorporate transgenes into the genetic material of the wild rice plant(s).

Expression Vectors for Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Selectable marker genes for plant transformation not of bacterial origin include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford et al., *Plant Physiol.* 86:1216 (1988); Jones et al., *Mol. Gen. Genet.*, 210:86 (1987); Svab et al., *Plant Mol. Biol.* 14:197 (1990); Hille et al., *Plant Mol. Biol.*

7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988).

Selectable marker genes for plant transformation not of bacterial origin include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS, β-galactosidase, luciferase and chloramphenicol acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984). Another approach to the identification of relatively rare transformation events has been use of a gene that encodes a dominant constitutive regulator of the *Zea mays* anthocyanin pigmentation pathway. Ludwig et al., *Science* 247:449 (1990).

In vivo methods for visualizing GUS activity that do not require destruction of plant tissue are available. Molecular Probes publication 2908, IMAGENE GREEN, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Expression Vectors for Transformation: Promoters

Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in wild rice. Optionally, the inducible promoter is operably linked to a nucleotide sequence encoding a signal sequence which is operably linked to a gene for expression in wild rice. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Meft et al., *PNAS* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

B. Constitutive Promoters—A constitutive promoter is operably linked to a gene for expression in wild rice or the constitutive promoter is operably linked to a nucleotide sequence encoding a signal sequence which is operably linked to a gene for expression in wild rice.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)).

The ALS promoter, Xbal/Ncol fragment 5' to the *Brassica napus* ALS3 structural gene (or a nucleotide sequence similarity to said Xbal/Ncol fragment), represents a particularly useful constitutive promoter. See PCT application WO96/30530.

C. Tissue-specific or Tissue-preferred Promoters—A tissue-specific promoter is operably linked to a gene for expression in wild rice. Optionally, the tissue-specific promoter is operably linked to a nucleotide sequence encoding a signal sequence which is operably linked to a gene for expression in wild rice. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-

3324 (1985)); a leaf-specific and light-induced promoter such as that from cab or rubisco (Simpson et al., *EMBO J.* 4(11):2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992); Close, P. S., Master's Thesis, Iowa State University (1993); Knox, C., et al., *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is wild rice. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant cultivar can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of wild rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper-accumulation of a monoterpene, a sesquiterpene, a steroid, a hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hornworm chitinase, and Kawalleck et al., Plant Molec. Biol. 21:673 (1993), who provide the nucleotide sequence of the parsley ubi4-2 polyubiquitin gene.

K. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., Plant Sci 89:43 (1993), of heterologous expression of a cecropin-β, lytic peptide analog to render transgenic tobacco plants resistant to Pseudomonas solanacearum.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., Nature 366:469 (1993), who show that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., Bio/Technology 10:1436 (1992). The cloning and characterization of a gene which encodes a bean endopolygalacturonase-inhibiting protein is described by Toubart et al., Plant J. 2:367 (1992).

R. A developmental-arrestive protein produced in nature by a plant. For example, Logemann et al., Bio/Technology 10:305 (1992), have shown that transgenic plants expressing the barley ribosome-inactivating gene have an increased resistance to fungal disease.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance conferred by mutant 5-enolpyruvlshikimate-3-phosphate synthase (EPSP) and aroA genes, respectively) and other phosphono compounds such as glufosinate (phosphinothricin acetyl transferase (PAT) and Streptomyces hygroscopicus PAT, bar, genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., Bio/Technology 7:61 (1989), describe the production of transgenic plants that express chimeric bar genes coding for PAT activity. Exemplary of genes conferring resistance to phenoxy propionic acids and cyclohexones, such as sethoxydim and haloxyfop are the Accl-S1, Accl-S2 and Accl-S3 genes described by Marshall et al., Theor. Appl. Genet. 83:435 (1992).

C. An herbicide that inhibits photosynthesis, such as a triazine (psbA and gs+ genes) or a benzonitrile (nitrilase gene). Przibilla et al., Plant Cell 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., Proc. Natl. Acad. Sci. U.S.A. 89:2624 (1992).

B. Decreased phytate content, 1) Introduction of a phytase-encoding gene would enhance breakdown of phytate, adding more free phosphate to the transformed plant. For example, see Van Hartingsveldt et al., Gene 127:87 (1993), for a disclosure of the nucleotide sequence of an Aspergillus niger phytase gene; 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., Maydica 35:383 (1990).

C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus mutants* fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus lichenifonnis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

Methods for Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

B. Direct Gene Transfer—Despite the fact the host range for *Agrobacterium*-mediated transformation is broad, some major cereal crop species and gymnosperms have generally been recalcitrant to this mode of gene transfer, even though some success has recently been achieved in wild rice and corn. Hiei et al., *The Plant Journal* 6:271-282 (1994) and U.S. Pat. No. 5,591,616 issued Jan. 7, 1997. Several methods of plant transformation collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Biotechnology* 10:268 (1992). In corn, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., *Bio/Technology* 9:996 (1991). Additionally, liposome and spheroplast fusion have been used to introduce expression vectors into plants. Deshayes et al., *EMBO J.,* 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994).

Following transformation of wild rice target tissues, expression of the above-described selectable marker genes allows for preferential selection of transformed cells, tissues and/or plants, using regeneration and selection methods now well known in the art.

The foregoing methods for transformation would typically be used for producing a transgenic cultivar. The transgenic cultivar could then be crossed, with another (non-transformed or transformed) cultivar, in order to produce a new transgenic cultivar. Alternatively, a genetic trait which has been engineered into a particular wild rice cultivar using the foregoing transformation techniques could be moved into another cultivar using traditional backcrossing techniques that are well known in the plant breeding arts. For example, a backcrossing approach could be used to move an engineered trait from a public, non-elite cultivar into an elite cultivar, or from a cultivar containing a foreign gene in its genome into a cultivar which does not contain that gene. As used herein, "crossing" can refer to a simple X by Y cross, or the process of backcrossing, depending on the context.

Single Gene Conversion

When the term wild rice plant is used in the context of the present invention, this also includes any single gene conversions of that cultivar. The term single gene converted plant as used herein refers to those wild rice plants which are developed by a plant breeding technique called backcrossing wherein essentially all of the desired morphological and physiological characteristics of a cultivar are recovered in addition to the single gene transferred into the cultivar via the backcrossing technique. Backcrossing methods can be used with the present invention to improve or introduce a characteristic into the cultivar. The term backcrossing as used herein refers to the repeated crossing of a hybrid progeny back to one of the parental wild rice plants, the recurrent parent, for that cultivar, i.e., backcrossing 1, 2, 3, 4, 5, 6, 7, 8, 9 or more times to the recurrent parent. The parental wild rice plant which contributes the gene for the desired characteristic is termed the nonrecurrent or donor parent. This terminology refers to the fact that the nonrecurrent parent is used one time in the backcross protocol and therefore does not recur. The parental wild rice plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second cultivar (nonrecurrent parent) that carries the single gene of interest to be transferred. The resulting progeny from this cross are then crossed again to the recurrent parent and the process is repeated until a wild rice plant is obtained wherein essentially all of the desired morphological and physiological characteristics of the recurrent parent are recovered in the converted plant, in addition to the single transferred gene from the nonrecurrent parent as determined at the 5% significance level when grown in the same environmental conditions.

The selection of a suitable recurrent parent is an important step for a successful backcrossing procedure. The goal of a backcross protocol is to alter or substitute a single trait or characteristic in the original cultivar. To accomplish this, a single gene of the recurrent cultivar is modified or substituted with the desired gene from the nonrecurrent parent, while retaining essentially all of the rest of the desired genetic, and therefore the desired physiological and morphological, constitution of the original cultivar. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new cultivar but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

Tissue Culture

Further reproduction of the variety can occur by tissue culture and regeneration. Tissue culture of various tissues of wild rice and regeneration of plants therefrom is well known and widely published. For example, reference may be had to Komatsuda, T. et al., Crop Sci. 31:333-337 (1991); Stephens, P. A., et al., Theor. Appl. Genet. (1991) 82:633-635; Komatsuda, T. et al., Plant Cell, Tissue and Organ Culture, 28:103-113 (1992); Dhir, S. et al., Plant Cell Reports (1992) 11:285-289; Pandey, P. et al., Japan J. Breed. 42:1-5 (1992); and Shetty, K., et al., Plant Science 81:245-251 (1992); as well as U.S. Pat. No. 5,024,944 issued Jun. 18, 1991 to Collins et al., and U.S. Pat. No. 5,008,200 issued Apr. 16, 1991 to Ranch et al. Thus, another aspect of this invention is to provide cells which upon growth and differentiation produce wild rice plants having the physiological and morphological characteristics of wild rice variety KC-755.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

As used herein, the term "plant" includes plant cells, plant protoplasts, plant cells of tissue culture from which wild rice plants can be regenerated, plant calli, plant clumps, and plant cells that are intact in plants or parts of plants, such as pollen, flowers, embryos, ovules, seeds, pods, leaves, stems, pistils, anthers and the like. Thus, another aspect of this invention is to provide for cells which upon growth and differentiation produce a cultivar having essentially all of the physiological and morphological characteristics of KC-755.

The present invention contemplates a wild rice plant regenerated from a tissue culture of a variety (e.g., KC-755) or hybrid plant of the present invention. As is well known in the art, tissue culture of wild rice can be used for the in vitro regeneration of a wild rice plant. Tissue culture of various tissues of wild rice and regeneration of plants therefrom is well known and widely published. For example, reference may be had to Chu, Q. R., et al., (1999) "Use of bridging parents with high anther culturability to improve plant regeneration and breeding value in rice", Rice Biotechnology Quarterly 38:25-26; Chu, Q. R., et al., (1998), "A novel plant regeneration medium for rice anther culture of Southern U.S. crosses", Rice Biotechnology Quarterly 35:15-16; Chu, Q. R., et al., (1997), "A novel basal medium for embryogenic callus induction of Southern US crosses", Rice Biotechnology Quarterly 32:19-20; and Oono, K., "Broadening the Genetic Variability By Tissue Culture Methods", Jap. J. Breed. 33 (Suppl.2), 306-307, illus. 1983. Thus, another aspect of this invention is to provide cells which upon growth and differentiation produce wild rice plants having the physiological and morphological characteristics of variety KC-755.

Duncan, et al., Planta 165:322-332 (1985) reflects that 97% of the plants cultured that produced callus were capable of plant regeneration. Subsequent experiments with both cultivars and hybrids produced 91% regenerable callus that produced plants. In a further study in 1988, Songstad, et al., Plant Cell Reports 7:262-265 (1988), reports several media additions that enhance regenerability of callus of two cultivars. Other published reports also indicated that "non-traditional" tissues are capable of producing somatic embryogenesis and plant regeneration. K. P. Rao et al., Maize Genetics Cooperation Newsletter, 60:64-65 (1986), refers to somatic embryogenesis from glume callus cultures and B. V. Conger, et al., Plant Cell Reports, 6:345-347 (1987) indicates somatic embryogenesis from the tissue cultures of corn leaf segments. Thus, it is clear from the literature that the state of the art is such that these methods of obtaining plants are routinely used and have a very high rate of success. Thus, another aspect of this invention is to provide cells which upon growth and differentiation produce wild rice plants having the physiological and morphological characteristics of wild rice cultivar KC-755.

Additional Breeding Methods

Although specific breeding objectives vary somewhat in the different regions, increasing yield is a primary objective in all programs. Grain yield of wild rice is determined by the number of panicles per unit area, the number of fertile florets per panicle, and grain weight per floret. Increases in any or all of these yield components may provide a mechanism to obtain higher yields. Heritable variation exists for all of these components, and breeders may directly or indirectly select for increases in any of them.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to low temperatures, and better grain quality including improve physical appearance, cooking and taste characteristics, and milling yield (% whole kernel milled wild rice or head wild rice and % total milled wild rice).

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection, or a combination of these methods.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from 8 to 12 years from the time the first cross is made and may rely on the development of improved breeding lines as precursors. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of wild rice plant breeding is to develop new, unique and superior wild rice cultivars and hybrids. The breeder initially selects and crosses two or more parental lines, followed by self-pollination and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same wild rice traits.

Each year, the plant breeder selects the germplasm to advance to the next generation. This germplasm is grown under unique and different geographical, climatic and soil conditions and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new wild rice cultivars.

The development of new wild rice cultivars requires the development and selection of wild rice varieties, the crossing of these varieties and selection of superior hybrid crosses. The hybrid seed is produced by manual crosses between selected male-fertile parents or by using male sterility or other systems. These hybrids are selected for certain single gene traits such as semi-dwarf plant type, pubescence, awns, and apiculus color which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin with evaluation of $F_1$ plants, continue with selection of $F_2$ plants, and on in the $F_3$, where the best individuals in the best families are selected and advanced. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, wild rice breeders commonly harvest one or more seeds from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh panicles with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987; Marshall and Wadsworth, 1994; Champagne, 2004).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

This invention also is directed to methods for producing a wild rice plant by crossing a first parent wild rice plant with a second parent wild rice plant wherein the first or second parent wild rice plant is a wild rice plant of the variety KC-755. Further, both first and second parent wild rice plants can come from the wild rice variety KC-755. Thus, any such methods using the wild rice variety KC-755 are part of this invention: selfing, backcrosses, hybrid production, crosses to populations, and the like. All plants produced using wild rice variety KC-755 as a parent are within the scope of this invention, including those developed from varieties derived from wild rice variety KC-755. Advantageously, the wild rice variety could be used in crosses with other, different, wild rice plants to produce the first generation ($F_1$) wild rice hybrid seeds and plants with superior characteristics. The variety of the invention can also be used for transformation where exogenous genes are introduced and expressed by the variety of the invention. Genetic variants created either through traditional breeding methods using variety KC-755 or through transformation of KC-755 by any of a number of protocols known to those of skill in the art are intended to be within the scope of this invention.

The following describes breeding methods that may be used with cultivar KC-755 in the development of further wild rice plants. One such embodiment is a method for developing an KC-755 progeny wild rice plant in a wild rice plant breeding program comprising: obtaining the wild rice plant, or a part thereof, of cultivar KC-755 utilizing said plant or plant part as a source of breeding material and selecting an KC-755 progeny plant with molecular markers in common with KC-755 and/or with morphological and/or physiological characteristics in common with KC-755. Breeding steps that may be used in the wild rice plant breeding program include pedigree breeding, back crossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of cultivar KC-755 progeny wild rice plants, comprising crossing cultivar KC-755 with another wild rice plant, thereby producing a population of wild rice plants, which, on average, derive 50% of their alleles from cultivar KC-755. A plant of this population may be selected and repeatedly selfed or sibbed with a wild rice cultivar resulting from these successive filial generations. One embodiment of this invention is the wild rice cultivar produced by this method and that has obtained at least 50% of its alleles from cultivar KC-755.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus the invention includes wild rice cultivar KC-755 progeny wild rice plants comprising a combination of at least two KC-755 traits so that said progeny wild rice plant is not significantly different for said traits than wild rice cultivar KC-755 as determined at the 5% significance level when grown in the same environment. Using techniques described herein, molecular markers may be used to identify said progeny plant as a KC-755 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of cultivar KC-755 may also be characterized through their filial relationship with wild rice cultivar KC-755, as for example, being within a certain number of breeding crosses of wild rice cultivar KC-755. A breeding cross is a cross made to introduce new genetics into the progeny, and is distinguished from a cross, such as a self or a sib cross, made to select among existing genetic alleles. The lower the number of breeding crosses in the pedigree, the closer the relationship between wild rice cultivar KC-755 and its progeny. For example, progeny produced by the methods described herein may be within 1, 2, 3, 4, 5, 6 or 7 breeding crosses of wild rice cultivar KC-755.

The seed of wild rice cultivar KC-755, the plant produced from the cultivar seed, the hybrid wild rice plant produced from the crossing of the cultivar, hybrid seed, and various parts of the hybrid wild rice plant and transgenic versions of the foregoing, can be utilized for human food, livestock feed, and as a raw material in industry, including fast-cooking wild rice made with a wet process, pre-cooked canned wild rice, pre-cooked shelf-stable wild rice, puffed kernels, broken kernels, meal, flour, oil, and nutracuetical products.

Tables

Table 2 shows the results of several trials comparing plant height in centimeters of wild rice cultivar KC-755 versus proprietary inbred lines B354 and R4 and synthetic line KC-F1B. Table 2, column 1 shows the variety name, column 2 shows the plant height results in centimeters for trial 1, which was a 2012 transplanted trial, column 3 shows the results for trial 2, which was a small-plot direct-seeded trial grown in 2012, column 4 shows the results of trial 3, which was a 2012 large-plot direct-seeded trial, column 5 shows the results of trial 4, which was a 2013 strip planting of subsamples, column 6 shows the results of trial 5, which was a 2013 single stem analysis samples, and column 7 shows the mean for each cultivar over all trials. Trials were planted in Pleasant Grove, Calif.

TABLE 2

| | Plant height (cm) | | | | | |
|---|---|---|---|---|---|---|
| Variety | Trial 1 | Trial 2 | Trial 3 | Trial 4 | Trial 5 | Mean |
| KC-755 | 158 | 175 | 158 | 203 | 188 | 176 |
| B354 | 178 | — | 193 | 255 | 237 | 216 |
| R4 | 183 | 195 | 190 | — | 208 | 194 |
| KC-F1B | 185 | 193 | 185 | 256 | 260 | 216 |
| MSE | 149.3 | 52.5 | 87.5 | | | |
| p | 0.13 | 0.038 | 0.046 | | | |

As shown in Table 2, KC-755 has a shorter plant height than inbred lines B354 and R4 and synthetic line KC-F1B.

Plant height in wild rice can be reduced directly by selecting genes for reduced stature or indirectly by shortening the growth cycle. Height reduction by shortening growth cycle can be detrimental to yield in already short-cycle crops because the shortened growth cycle limits biomass production and grain yield. The commercial open-pollinated wild rice variety, 'Franklin' is an example. Franklin is a shorter variety, but mainly because of its short growth cycle. KC-755, conversely, maintains its growth cycle despite its reduction in plant height (see Table 4). The growth cycle of KC-755 is shown in Table 3 below.

TABLE 3

| Growth stage | Number of days |
|---|---|
| Seed germination and seedling establishment (seedlings completely or partially submerged) | 25 |
| Vegetative growth and reproductive growth initiation | 25-30 |
| Reproductive growth and grain filling | 40 |
| Grain filling and maturation | 20 |
| Total number of days | 110-115 |

As shown in Table 3, the purely vegetative growth period (predominantly leaf and tiller production) is only 25-30 days. Before this, growth is slow because the seedlings are completely or partially submerged in water. Muddy or murky water can occur frequently, which reduces light penetration into the water, further limiting growth rate during this stage. Late in the 25-30 day "vegetative" period, reproductive growth begins to compete with vegetative plant development. The achievement of substantial height reduction in KC-755 without shortening its cycle preserves the vegetative stage critical for plant and leaf canopy development.

Table 4 shows a comparison of height reduction of KC-755 versus commercial variety Franklin, inbred lines B354 and R4, and synthetic line KC-F1B as related to cycle length. Table 4, column 1 shows the variety name, column 2 shows the number of days to 50% heading, and column 3 shows the plant height in centimeters (cm) for a trial planted in Pleasant Grove, Calif. in 2012.

TABLE 4

| Variety | Days to 50% heading | Plant height (cm) |
|---|---|---|
| KC-755 | 58.5 | 158 |
| Franklin | 46.0 | 148 |
| B354 | 58.0 | 192 |
| R4 | 58.0 | 190 |
| KC-F1B | 57.5 | 185 |
| MSE | 0.833 | 87.5 |
| p | <0.01 | $0.01 < p < 0.05$ |

As shown in Table 4, wild rice cultivar KC-755 of the present invention is agronomically significantly shorter than other wild rice controls of similar maturity. These results further show that wild rice KC-755 attains its reduced stature without compromising its vital vegetative growth cycle. Additionally, information from field observations in 2013 show that KC-755 has much lower lodging than a leading commercial synthetic variety (KC-F1B) grown under similar fertility conditions.

The elongated stem of a mature wild rice plant is constructed of internodes separated by nodes, leaves, and leaf sheaths. The number and relative lengths of the internodes, including panicles, together with sheath lengths and leaf size and angles collectively define the plant architecture or shape of the plant. It is important that height reduction does not come at the expense of reduced panicle size or distortions of the canopy that are detrimental to competitive growth and yield.

Table 5 shows the results of an analysis of internode elongation patterns for wild rice cultivar KC-755 versus proprietary inbred lines B354 and R4 and commercial synthetic variety KC-F1B. Thirty stem samples were drawn from large production blocks grown under commercial conditions in California. Table 5, column 1 shows the variety, column 2 shows the total height in centimeters (cm), column 3 shows the panicle length in cm, column 4 shows the panicle length percent (%), column 5 shows the peduncle ($I_1$) length in cm, column 6 shows the peduncle ($I_1$) length percent (%), column 7 shows the other internodes ($I_2$-$I_5$) length in cm, column 8 shows the other internodes ($I_2$-$I_5$) length percent (%), and column 9 shows the number of elongated internodes. Data in Table 5 are from 2013 in Sutter County, California.

TABLE 5

| Variety | Total height (cm) | Panicle length (cm) | Panicle length (%) | Peduncle ($I_1$) $I_1$ length (cm) | $I_1$ length (%) | Other internodes $I_2$-$I_5$ length (cm) | $I_2$-$I_5$ length (%) | No. elongated internodes |
|---|---|---|---|---|---|---|---|---|
| KC-755 | 188 | 50.9 | 27.2 | 84.7 | 45.2 | 51.7 | 27.4 | 4.0 |
| B354 | 237 | 45.3 | 19.1 | 99.6 | 42.1 | 93.3 | 39.3 | 4.7 |
| R4 | 208 | 54.2 | 26.0 | 97.8 | 47.0 | 57.2 | 27.4 | 4.2 |
| KC-F1B | 260 | 48.6 | 18.7 | 104.5 | 40.2 | 108.0 | 41.5 | 4.6 |

As shown in Table 5, primary stems of wild rice cultivar KC-755 ranged from 20 to 72 cm shorter than three controls. KC-755 had slightly fewer elongated internodes (4.0) compared to the controls (mean=4.5) and the panicle length was similar for all entries. The peduncle, the longest single internode in most wild rice germplasm, was significantly reduced in length in KC-755, averaging 13 to 20 cm less than the controls. Remaining internodes, $I_2$-$I_5$, were also reduced in KC-755, measuring from 5.5 to 56.3 cm. shorter than the controls. These results show that KC-755 achieves its height reduction primarily by having shortened basal internodes $I_2$-$I_5$, and secondarily by reducing the peduncle length.

All current commercial wild rice varieties have a high degree of panicle exsertion, i.e. a substantial length and proportion of the peduncle is exposed between the panicle and flag leaf sheath. This elongated internode is deleterious for commercial production because it adds significant leverage to the forces that cause lodging, primarily wind and rain, but including the grain weight. The normal phenotype of wild rice is similar to the eui, elongated upper internode phenotype mutants described in rice. Length reduction of this internode could help reduce lodging, a chronic problem in wild rice production. Table 6 shows a comparison of panicle exsertion of wild rice cultivar KC-755 versus proprietary inbred lines B354 and R4 and commercial synthetic variety KC-F1B. Table 6, column 1 shows the variety, column 2 shows the total height in centimeters (cm), column 3 shows the peduncle ($I_1$) length in cm, column 4 shows the flag leaf sheath length in cm, column 5 shows the panicle exsertion in cm, and column 6 shows the panicle exsertion percent. Data in Table 6 are from 2013 in Pleasant Grove, Calif.

TABLE 6

| Variety | Total height (cm) | Peduncle ($I_1$) length (cm) | Flag leaf sheath length (cm) | Panicle exsertion (cm) | Panicle exsertion (%) |
|---|---|---|---|---|---|
| KC-755 | 188 | 82.4 | 52.7 | 29.7 | 36.0 |
| B354 | 237 | 102.9 | 55.5 | 47.4 | 46.1 |
| R4 | 208 | 97.8 | 56.1 | 41.7 | 42.6 |
| KC-F1B | 260 | 104.0 | 56.8 | 47.2 | 45.4 |

As shown in Table 6, panicle exsertion of wild rice KC-755 is between 12 to nearly 18 cm less than the controls. The observed panicle exsertion is a lower percentage of the entire plant height as well. These results further show that wild rice cultivar KC-755 has a more compact plant structure in terms of panicle exsertion. This "drawing in" of the panicle more into the canopy may account for the lodging resistance of KC-755 observed in large scale plantings.

Leaf size and angle are important components of a crop canopy. For wild rice, more erect leaf types are desired for commercial production because they allow the higher population of commercial planting to achieve good light distribution and enhance yields. Panicle branching angles were considered separately for the male and female portions of the panicle. Branching angles were measured in degrees as a departure from vertical. A low female branching angle (FBA) is desirable because all the grains are thereby held closely along the rachis, thus being somewhat protected from shattering loss due to wind and losses due to bird predation. Female branching angles can be as high as 90°. Plants having FBA more than 15-30 degrees are considered to have "crow foot."

Male branching angles (MBA) may also be important, but not for preventing grain loss. A widely branched male may create more shadowing of the photosynthetically important leaves beneath the panicle, although the effect is probably minor. More importantly, a general correlation between male branching angle and female branching angle has been observed, with a low MBA nearly always associated with the desired low FBA. Table 7 shows a comparison of leaf and panicle branching characteristics of wild rice cultivar KC-755 versus proprietary inbred lines B354 and R4 and commercial synthetic variety KC-F1B. Table 7, column 1 shows the variety, column 2 shows the flag leaf length in centimeters (cm), column 3 shows the flag leaf width in cm, column 4 shows the flag leaf angle measured in degrees from vertical, column 5 shows the penultimate leaf angle measured in degrees from vertical, column 6 shows the panicle female branch angle (FBA) measured in degrees from vertical, and column 7 shows the male branch angle (MBA) measured in degrees from vertical. Data in Table 7 are from 2013 in Pleasant Grove, Calif.

TABLE 7

| | Flag leaf | | | Penultimate leaf | Panicle | |
|---|---|---|---|---|---|---|
| Variety | Length (cm) | Width (cm) | Angle | Angle | FBA | MBA |
| KC-755 | 33.4 | 2.60 | 13.6 | 15.3 | 2.2 | 22.2 |
| B354 | 36.1 | 2.72 | 56.1 | 40.0 | 11.6 | 53.7 |
| R4 | 44.7 | 3.11 | 19.8 | 15.8 | 9.0 | 42.5 |
| KC-F1B | 34.8 | 2.81 | 30.3 | 28.0 | 8.8 | 52.0 |

As shown in Table 7, flag leaves of wild rice cultivar KC-755 are similar in size to B354 and KC-F1B, but may be smaller than those of R4. However, the display angles of the upper two, most photosynthetically active, leaves of KC-755 are very acute. Leaf angles of KC-755 are similar to, but less than R4, and much less than B354 and KC-F1B. The female panicle branches in KC-755 are tightly appressed to the rachis and therefore have a very desirable, low FBA. The MBA of KC-755 is markedly less than that of the controls. Thus, both FBA and MBA of KC-755 are lower than the controls. The low MBA of KC-755 is also useful as a phenotypic marker for identification purposes. These results further show that KC-755 has very erect leaf display characteristics, creating a desirable plant canopy and excellent panicle morphology for minimizing shattering and predation loss.

Harvest index (HI) is an important measure of the efficiency in converting dry matter production into grain. Wild progenitors of grain crops and unimproved varieties have low harvest indices. Wild rice is a partially domesticated species, having only been in cultivation for less than 50 years. HI of 15% to low 20's has been reported for wild rice.

Increased HI is valuable because it increases grain yield without increasing dry matter production. This is a desirable attribute, because increasing dry matter production usually requires increased crop production inputs. Varieties with HI as high as 50% are available in highly developed crop species such as Oryza rice. Conventionally tall inbred lines and varieties of wild rice have HI percentages in the low 20's.

Table 8 shows the harvest index (HI) of wild rice cultivar KC-755 versus proprietary inbred line B354 and commercial synthetic variety KC-F1B from a trial grown in 2013 in Pleasant Grove, Calif. Table 8, column 1 shows the variety, column 2 shows the grain weight in grams (g), column 3 shows the total vegetative weight in g, and column 4 shows the harvest index (HI).

TABLE 8

| Variety | Grain weight (g) | Total vegetative weight (g) | Harvest Index |
| --- | --- | --- | --- |
| KC-755 | 75 | 187 | 28.6% |
| B354 | 58 | 182 | 24.2% |
| KC-F1B | 53 | 207 | 20.4% |

As shown in Table 8, wild rice cultivar KC-755 has an improved HI when compared to the controls. Wild rice cultivar KC-755, which has a reduced plant height while maintaining panicle size, has an HI of 28.6%, whereas inbred line B354 and commercial synthetic variety KC-F1B have an HI of 24.2% and 20.4%, respectively.

Published information on wild rice yield in California is scarce. However, one public study compared five open pollinated varieties at two locations in California (Williams, 1998). The overall average yield was 1,306 lb per acre on field-run green paddy. Only one of the five varieties in the study, Franklin, is still grown commercially in California. In the mentioned study, Franklin averaged 1,229 lb/acre.

These yields are low compared to other irrigated grain crops, a reflection of the newness of wild rice as a crop. The yield information serves as a baseline for comparison to yield of current populations, lines, and varieties, particularly KC-755. Table 9 shows the results of two trials grown in Pleasant Grove, Calif. in 2012 for wild rice cultivar KC-755 versus proprietary inbred lines B354 and R4, commercial synthetic variety KC-F1B, and open pollinated commercial variety Franklin. Table 9, column 1 shows the variety name, column 2 shows the grain yield in kg/ha for trial 1 grown in 3 m² plots, column 3 shows the grain yield in kg/ha for trial 2 grown in 1.5 m² plots, and column 4 shows the mean between the two trials in kg/ha.

TABLE 9

| | 2012 Grain yield (kg/ha) | | |
| --- | --- | --- | --- |
| Variety | Trial 1 3 m² plots | Trial 2 1.5 m² plots | Mean |
| KC-755 | 2,545 | 3,526 | 3,036 |
| B354 | 2,863 | — | — |
| R4 | 2,858 | 1,628 | 2,243 |
| KC-F1B | 2,571 | 1,924 | 2,247 |
| Franklin | 1,764 | — | — |
| MSE | 261,090 | — | — |
| p | 0.32 | — | — |

As shown in Table 9, when wild rice cultivar KC-755 was compared to Franklin in one trial, KC-755 out-yielded Franklin by 781 kg/ha, which is a yield differential of 44%; however, the results were not statistically significant. Wild rice cultivar KC-755 also showed a higher yield than R4 and KC-F1B.

Table 10 shows the results of samples from large commercial-scale production blocks grown in California in 2013 for wild rice cultivar KC-755 versus proprietary inbred lines B354 and R4, and commercial synthetic variety KC-F1B. Table 10, column 1 shows the variety name, column 2 shows the location where LO indicates Live Oak, Calif. and PLG indicates Pleasant Grove, Calif., column 3 shows the grain yield in kg/ha for results based on quadruplicate 1.5 m² samples and presented at 30% moisture, and column 4 shows the standard error of the mean.

TABLE 10

| Variety | Location | Grain yield (kg/ha) | $S_x$ |
| --- | --- | --- | --- |
| KC-755 | LO | 3,256 | 212 |
| KC-755 | PLG | 3,547 | 228 |
| B354 | PLG | 2,107 | 188 |
| R4 | PLG | 2,500 | 228 |
| KC-F1B | LO | 2,651 | 314 |
| KC-F1B | PLG | 2,626 | 198 |

As shown in Table 10, wild rice cultivar KC-755 out-yielded the two inbred lines B354 and R4 by 48% and out-yielded the commercial synthetic variety KC-F1B by 29%. These results show that wild rice cultivar KC-755 of the present invention has superior commercial yield potential as a variety.

Kernel size is an important quality characteristic in wild rice. Wild rice varieties tend to be quite variable for many traits, kernel weight and length included. Kernel length is an important quality characteristic for marketing processed wild rice, with longer kernels earning a market premium. Cultivated wild rice seed sizes are quite variable because of the semi-domesticated status of the crop. No current variety produces a preponderance of premium grades, so processed wild rice is normally graded to extract whatever premium grades might be present. A variety with reliably increased production of large, long kernels would be a benefit to the industry.

Table 11 shows the results for kernel size and shape characteristics of wild rice cultivar KC-755 versus proprietary inbred lines B354 and R4, and commercial synthetic variety KC-F1B in a 2012 transplanted trial grown in Pleasant Grove, Calif. Table 11, column 1 shows the variety, column 2 shows the kernel weight in milligrams (mg), column 3 shows the kernel length in millimeters (mm), column 4 shows the kernel width in mm, and column 5 shows the length to width (L:W) ratio.

TABLE 11

| Variety | Kernel weight (mg) | Kernel length (mm) | Kernel width (mm) | L:W ratio |
| --- | --- | --- | --- | --- |
| KC-755 | 33.8 | 11.1 | 1.68 | 6.63 |
| B354 | 32.1 | 10.0 | 1.72 | 5.82 |
| R4 | 34.8 | 10.8 | 1.77 | 6.14 |
| KC-F1B | 32.0 | 9.9 | 1.72 | 5.77 |
| MSE | 4.367 | 0.0725 | 0.0037 | 0.0134 |
| p | 0.57 | <0.01 | 0.78 | <0.01 |
| $LSD_{0.05}$ | NS | | NS | |

As shown in Table 11, wild rice cultivar KC-755, the two inbred controls B354 and R4, and commercial synthetic KC-F1B were not significantly different for kernel weight and kernel width. Kernels of KC-755 were significantly longer and more slender than KC-F1B and B354, but only slightly more so than R4.

Table 12 shows the results of a second set of samples drawn in 2012 from larger seed production blocks grown in Pleasant Grove, Calif. under commercial conditions for wild rice cultivar KC-755 versus proprietary inbred lines B354 and R4, and commercial synthetic variety KC-F1B. Table 12, column 1 shows the variety, column 2 shows the kernel weight in milligrams (mg), column 3 shows the kernel length in millimeters (mm), column 4 shows the kernel width in mm, and column 5 shows the length to width (L:W) ratio.

TABLE 12

| Variety | Kernel weight (mg) | Kernel length (mm) | Kernel width (mm) | L:W ratio |
|---|---|---|---|---|
| KC-755 | 31.6 | 10.3 | 1.76 | 5.89 |
| B354 | 23.2 | 8.4 | 1.71 | 4.98 |
| R4 | 29.2 | 9.9 | 1.78 | 5.56 |
| KC-F1B | 26.6 | 9.8 | 2.11 | 4.67 |
| MSE | 5.566 | 0.0400 | 0.0095 | 0.1648 |
| df error | 5 | 4 | 4 | 4 |
| p | 0.047 | <0.01 | 0.046 | |
| $LSD_{0.05}$ | | | | NS |

As shown in Table 12, wild rice cultivar KC-755 had a higher kernel weight and longer kernel length than inbred controls B354 and R4 and synthetic variety KC-F1B. The length to width ratio narrowly favored wild rice cultivar KC-755 over R4.

Table 13 shows the results of a third set of samples drawn in 2013 from large seed production blocks grown in California under commercial conditions for wild rice cultivar KC-755 versus proprietary inbred lines B354 and R4, and commercial synthetic variety KC-F1B. Table 13, column 1 shows the variety, column 2 shows the location, where LO indicates Live Oak, Calif., PLG indicates Pleasant Grove, Calif., and YC indicates Yolo County, California, column 3 shows the kernel weight in milligrams (mg), column 4 shows the kernel length in millimeters (mm), column 5 shows the kernel width in mm, and column 6 shows the length to width (L:W) ratio.

TABLE 13

| Variety | Location | Kernel weight (mg) | Kernel length (mm) | Kernel width (mm) | L:W ratio |
|---|---|---|---|---|---|
| KC-755 | LO | 28.5 | 10.3 | 2.04 | 5.05 |
| KC-755 | PLG | 34.9 | 11.3 | 1.72 | 6.59 |
| KC-755 | PLG | 31.3 | 10.5 | 1.70 | 6.18 |
| B354 | PLG | 22.1 | 8.3 | 1.66 | 5.00 |
| R4 | PLG | 35.4 | 22.5 | 1.78 | 6.44 |
| KC-F1B | LO | 26.2 | 9.3 | 2.13 | 4.38 |
| KC-F1B | PLG | 24.2 | 8.9 | 1.99 | 4.48 |
| KC-F1B | YC | 25.0 | 9.0 | 1.60 | 5.64 |

As shown in Table 13, wild rice cultivar KC-755 produced heavier, longer and more slender kernels than the controls.

Table 14 shows the results when the three trials presented in Tables 11-13 are combined. Table 14, column 1 shows the variety, column 2 shows the number of observations, column 3 shows the kernel weight in milligrams (mg), column 4 shows the kernel length in millimeters (mm), column 5 shows the kernel width in mm, and column 6 shows the length to width (L:W) ratio.

TABLE 14

| Variety | No. observations | Kernel weight (mg) | Kernel length (mm) | Kernel width (mm) | L:W ratio |
|---|---|---|---|---|---|
| KC-755 | 4 | 32.6 | 11.1 | 1.92 | 5.78 |
| B354 | 3 | 25.6 | 9.1 | 1.83 | 4.99 |
| R4 | 4 | 33.1 | 10.7 | 1.78 | 6.05 |
| KC-F1B | 4 | 27.2 | 9.6 | 2.08 | 4.61 |

As shown in Table 14, when the three trials are combined, wild rice cultivar KC-755 shows significant superiority to inbred line B354 and synthetic variety KC-F1B in kernel weight and kernel length and an increase in kernel length and length to width ratio compared to inbred line R4. Collectively these data show that wild rice cultivar KC-755 produces kernels that are significantly larger (both weight and length) and more slender (higher L:W ratio) than the commercial KC-F1B synthetic and the inbred line B354, and slightly larger than the inbred line R4. Wild rice cultivar KC-755, because of its possible direct use in commercial production, represents a significant quality upgrade compared to a current commercial cultivar KC-F1B. Because of its large kernel size, KC-755 should also be useful as a parent in synthetic and/or hybrid varieties.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Deposit Information

A deposit of the Kennan Corporation proprietary Wild Rice Cultivar KC-755 disclosed above and recited in the appended claims has been made with the American Type Culture Collection (ATCC), 10801 University Boulevard, Manassas, Va. 20110. The date of deposit was Jan. 30, 2014. The deposit of 2,500 seeds was taken from the same deposit maintained by Kennan Corporation since prior to the filing date of this application. All restrictions will be irrevocably removed upon granting of a patent, and the deposit is intended to meet all of the requirements of 37 C.F.R. §§1.801-1.809. The ATCC Accession Number is PTA-120953. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A seed of rice cultivar KC-755, wherein a representative sample of seed of said cultivar has been deposited under ATCC Accession No. PTA-120953.

2. A rice plant, or a part thereof, produced by growing the seed of claim 1.

3. A tissue culture of cells produced from the plant of claim 2, wherein said cells of the tissue culture are produced from a plant part selected from the group consisting of leaf, pollen, embryo, cotyledon, hypocotyl, meristematic cell, root, root tip, pistil, anther, flower, stem, glumes and panicle.

4. A protoplast produced from the plant of claim 2.

5. A protoplast produced from the tissue culture of claim 3.

6. A rice plant regenerated from the tissue culture of claim 3, wherein the plant has all of the morphological and physiological characteristics of rice cultivar KC-755.

7. A method for producing an $F_1$ hybrid rice seed, wherein the method comprises crossing the plant of claim 2 with a different rice plant and harvesting the resultant $F_1$ hybrid rice seed.

8. A hybrid rice seed produced by the method of claim 7.

9. A hybrid rice plant, or a part thereof, produced by growing said hybrid rice seed of claim 8.

10. A method of producing an herbicide resistant rice plant, wherein the method comprises transforming the rice plant of claim 2 with a transgene, wherein the transgene confers resistance to an herbicide selected from the group consisting of imidazolinone, sulfonylurea, glyphosate, glufosinate, L-phosphinothricin, triazine and benzonitrile.

11. An herbicide resistant rice plant produced by the method of claim 10.

12. A method of producing an insect resistant rice plant, wherein the method comprises transforming the rice plant of claim 2 with a transgene that confers insect resistance.

13. An insect resistant rice plant produced by the method of claim 12.

14. The rice plant of claim 13, wherein the transgene encodes a *Bacillus thuringiensis* endotoxin.

15. A method of producing a disease resistant rice plant, wherein the method comprises transforming the rice plant of claim 2 with a transgene that confers disease resistance.

16. A disease resistant rice plant produced by the method of claim 15.

17. A method of producing a rice plant with modified fatty acid metabolism or modified carbohydrate metabolism, wherein the method comprises transforming the rice plant of claim 2 with a transgene encoding a protein selected from the group consisting of fructosyltransferase, levansucrase, alpha-amylase, invertase and starch branching enzyme or DNA encoding an antisense of stearyl-ACP desaturase.

18. A rice plant having modified fatty acid metabolism or modified carbohydrate metabolism produced by the method of claim 17.

19. A method of introducing a desired trait into rice cultivar KC-755, wherein the method comprises:
 (a) crossing a KC-755 plant, wherein a representative sample of seed was deposited under ATCC Accession No. PTA-120953, with a plant of another rice cultivar that comprises a desired trait to produce progeny plants, wherein the desired trait is selected from the group consisting of male sterility, herbicide resistance, insect resistance, abiotic stress tolerance, modified fatty acid metabolism, modified carbohydrate metabolism and resistance to bacterial disease, fungal disease or viral disease;
 (b) selecting one or more progeny plants that have the desired trait;
 (c) backcrossing the selected progeny plants with the KC-755 plants to produce backcross progeny plants;
 (d) selecting for backcross progeny plants that have the desired trait; and
 (e) repeating steps (c) and (d) two or more times to produce selected third or higher backcross progeny plants that comprise the desired trait.

20. A plant produced by the method of claim 19, wherein the plant has the desired trait and all of the physiological and morphological characteristics of rice cultivar KC-755.

21. The plant of claim 20, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

22. The plant of claim 20, wherein the desired trait is insect resistance and the insect resistance is conferred by a transgene encoding a *Bacillus thuringiensis* endotoxin.

23. The plant of claim 20, wherein the desired trait is modified fatty acid metabolism or modified carbohydrate metabolism and said desired trait is conferred by a nucleic acid encoding a protein selected from the group consisting of fructosyltransferase, levansucrase, alpha-amylase, invertase and starch branching enzyme or DNA encoding an antisense of stearyl-ACP desaturase.

24. The plant of claim 20, wherein the desired trait is abiotic stress tolerance and said desired trait modifies tolerance to drought, flooding, salinity, or temperature change.

25. A method of producing a commodity plant product, comprising obtaining the plant of claim 2, or a part thereof, and producing the commodity plant product from said plant or plant part thereof, wherein said commodity plant product is selected from the group consisting of fast-cooking wild rice made with a wet process, pre-cooked canned wild rice, pre-cooked shelf-stable wild rice, puffed kernels, broken kernels, meal, flour, oil, and nutracuetical products.

* * * * *